United States Patent [19]

Olson et al.

[11] Patent Number: 5,991,656
[45] Date of Patent: Nov. 23, 1999

[54] PRIORITIZED RULE BASED APPARATUS FOR DIAGNOSIS AND TREATMENT OF ARRHYTHMIAS

[75] Inventors: Walter H. Olson, North Oaks; William F. Kaemmerer, Edina, both of Minn.

[73] Assignee: Medtronic, Inc., Minneapolis, Minn.

[21] Appl. No.: 09/158,699

[22] Filed: Sep. 22, 1998

Related U.S. Application Data

[62] Division of application No. 08/874,067, Jun. 12, 1997, Pat. No. 5,855,593, which is a continuation of application No. 08/633,254, Jun. 19, 1996, abandoned, which is a continuation of application No. 08/413,570, Mar. 30, 1995, Pat. No. 5,545,186.

[51] Int. Cl.$^6$ .................................................... A61N 1/362
[52] U.S. Cl. .................................................. 607/4; 607/14
[58] Field of Search .................................... 607/4, 5, 9, 14

[56] References Cited

U.S. PATENT DOCUMENTS

| 4,799,793 | 1/1989 | Dufault . |
| 5,086,772 | 2/1992 | Larnard . |
| 5,184,615 | 2/1993 | Nappholz . |
| 5,193,535 | 3/1993 | Bardy . |
| 5,330,508 | 7/1994 | Gunderson . |
| 5,545,186 | 8/1996 | Olson et al. ........................ 607/14 |

FOREIGN PATENT DOCUMENTS

| 0617980 | 10/1994 | European Pat. Off. . |
| 0253505 | 1/1998 | European Pat. Off. . |
| 9302746 | 2/1993 | WIPO . |
| 9419054 | 9/1994 | WIPO . |

*Primary Examiner*—William E. Kamm
*Assistant Examiner*—George R. Evanisho
*Attorney, Agent, or Firm*—Reed A. Duthler; Harold R. Patton

[57] ABSTRACT

An implantable antiarrhythmia device which detects and classifies arrhythmias of the human heart, and delivers appropriate therapy. The device employs a method of arrhythmia classification based on a set of prioritized rules, each of the rules defining a plurality of criteria based upon characteristics of sensed depolarizations of heart tissue, each rule being met when the criteria associated with the rule are met. Some rules, when met, trigger delivery of antiarrhythmia therapy. Other rules, when met, inhibit delivery of antiarrhythmia therapy. The rules may be met simultaneously, and if so, the highest priority rule governs the behavior of the device.

7 Claims, 11 Drawing Sheets

| PRIOR R EVENT BEAT CODE: | CURRENT R EVENT BEAT CODE: | | | | | | | | | |
|---|---|---|---|---|---|---|---|---|---|---|
| | 0 | 1 | 2 | 3 | 4 | 5 | 6 | 7 | 8 | 9 |
| 0 | 0 [A] | 18 [Z] | 11 [L] | 18 [Z] | 14 [O] | 14 [O] | 14 [O] | 1 [B] | 17 [Y] | 3 [D] |
| 1 | 18 [Z] | 5 [F] | 18 [Z] | 18 [Z] | 14 [O] | 14 [O] | 14 [O] | 18 [Z] | 17 [Y] | 14 [O] |
| 2 | 12 [M] | 18 [Z] | 6 [G] | 18 [Z] | 14 [O] | 14 [O] | 14 [O] | 10 [K] | 17 [Y] | 14 [O] |
| 3 | 18 [Z] | 18 [Z] | 18 [Z] | 13 [N] | 14 [O] | 14 [O] | 14 [O] | 18 [Z] | 17 [Y] | 14 [O] |
| 4 | 15 [P] | 15 [P] | 15 [P] | 15 [P] | 16 [Q] | 16 [Q] | 16 [Q] | 18 [Z] | 17 [Y] | 16 [Q] |
| 5 | 15 [P] | 15 [P] | 15 [P] | 15 [P] | 16 [Q] | 16 [Q] | 16 [Q] | 7 [H] | 17 [Y] | 16 [Q] |
| 6 | 15 [P] | 15 [P] | 15 [P] | 15 [P] | 16 [Q] | 16 [Q] | 16 [Q] | 18 [Z] | 17 [Y] | 16 [Q] |
| 7 | 18 [Z] | 9 [J] | 18 [Z] | 18 [Z] | 2 [C] | 8 [I] | 18 [Z] | 18 [Z] | 18 [Z] | 2 [C] |
| 8 | 17 [Y] | 17 [Y] | 17 [Y] | 17 [Y] | 17 [Y] | 17 [Y] | 17 [Y] | 18 [Z] | 17 [Y] | 17 [Y] |
| 9 | 4 [E] | 15 [P] | 15 [P] | 15 [P] | 16 [Q] | 16 [Q] | 16 [Q] | 18 [Z] | 17 [Y] | 16 [Q] |

FIG. 5

| PATTERN CODE: | CURRENT STATE: | | | | | | | | | |
|---|---|---|---|---|---|---|---|---|---|---|
| | 0 [RESET] | 19 [A] | 38 [B] | 57 [CD] | 76 [E] | 95 [A1] | 114 [A2] | 133 [L] | 152 [M] | 171 [Z] |
| [A] 0 | 19 | 19 | 0 | 0 | 114 | 114 | 19 | 0 | 95 | 95 |
| [B] 1 | 38 | 38 | 0 | 0 | 0 | 0 | 0 | 0 | 0 | 0 |
| [C] 2 | 57 | 0 | 57 | 0 | 0 | 0 | 0 | 0 | 0 | 0 |
| [D] 3 | 57 | 57 | 0 | 0 | 0 | 0 | 0 | 0 | 0 | 0 |
| [E] 4 | 76 | 0 | 0 | 76 | 0 | 0 | 0 | 0 | 0 | 0 |
| [F] 5 | 0 | 0 | 0 | 0 | 0 | 0 | 0 | 0 | 0 | 0 |
| [G] 6 | 0 | 0 | 0 | 0 | 0 | 0 | 0 | 0 | 0 | 0 |
| [H] 7 | 0 | 0 | 0 | 0 | 0 | 0 | 0 | 0 | 0 | 0 |
| [I] 8 | 0 | 0 | 0 | 0 | 0 | 0 | 0 | 0 | 0 | 0 |
| [J] 9 | 0 | 0 | 0 | 0 | 0 | 0 | 0 | 0 | 0 | 0 |
| [K] 10 | 0 | 0 | 0 | 0 | 0 | 0 | 0 | 0 | 0 | 0 |
| [L] 11 | 133 | 133 | 0 | 0 | 0 | 0 | 0 | 0 | 0 | 0 |
| [M] 12 | 152 | 0 | 0 | 0 | 0 | 0 | 0 | 152 | 0 | 0 |
| [N] 13 | 0 | 0 | 0 | 0 | 0 | 0 | 0 | 0 | 0 | 0 |
| [O] 14 | 0 | 0 | 0 | 0 | 0 | 0 | 0 | 0 | 0 | 0 |
| [P] 15 | 0 | 0 | 0 | 0 | 0 | 0 | 0 | 0 | 0 | 0 |
| [Q] 16 | 0 | 0 | 0 | 0 | 0 | 0 | 0 | 0 | 0 | 0 |
| [Y] 17 | 0 | 0 | 0 | 0 | 0 | 0 | 0 | 0 | 0 | 0 |
| [Z] 18 | 171 | 0 | 171 | 0 | 0 | 0 | 0 | 0 | 0 | 0 |

FIG. 6

| PATTERN CODE: | CURRENT STATE: | | | | | | | | | | |
|---|---|---|---|---|---|---|---|---|---|---|---|
| | [RESET] 0 | [O] 19 | [P1] 38 | [P2] 57 | [Q] 76 | [L] 95 | [M] 114 | [A] 133 | [N1] 152 | [N2] 171 | [Z1] 190 | [Z2] 209 |
| [A] 0 | 133 | 0 | 133 | 0 | 0 | 0 | 0 | 0 | 0 | 0 | 0 | 0 |
| [B] 1 | 0 | 0 | 0 | 0 | 0 | 0 | 0 | 0 | 0 | 0 | 0 | 0 |
| [C] 2 | 0 | 0 | 0 | 0 | 0 | 0 | 0 | 0 | 0 | 0 | 0 | 0 |
| [D] 3 | 0 | 0 | 0 | 0 | 0 | 0 | 0 | 0 | 0 | 0 | 0 | 0 |
| [E] 4 | 0 | 0 | 0 | 0 | 0 | 0 | 0 | 0 | 0 | 0 | 0 | 0 |
| [F] 5 | 0 | 0 | 0 | 0 | 0 | 0 | 0 | 0 | 0 | 0 | 0 | 0 |
| [G] 6 | 0 | 0 | 0 | 0 | 0 | 0 | 0 | 0 | 0 | 0 | 0 | 0 |
| [H] 7 | 0 | 0 | 0 | 0 | 0 | 0 | 0 | 0 | 0 | 0 | 0 | 0 |
| [I] 8 | 0 | 0 | 0 | 0 | 0 | 0 | 0 | 0 | 0 | 0 | 0 | 0 |
| [J] 9 | 0 | 0 | 0 | 0 | 0 | 0 | 0 | 0 | 0 | 0 | 0 | 0 |
| [K] 10 | 0 | 0 | 0 | 0 | 0 | 0 | 0 | 0 | 0 | 0 | 0 | 0 |
| [L] 11 | 95 | 0 | 95 | 0 | 0 | 0 | 0 | 0 | 0 | 0 | 0 | 0 |
| [M] 12 | 114 | 0 | 0 | 0 | 0 | 114 | 0 | 0 | 0 | 0 | 0 | 0 |
| [N] 13 | 152 | 0 | 152 | 171 | 0 | 0 | 0 | 171 | 171 | 0 | 171 | 0 |
| [O] 14 | 19 | 0 | 19 | 19 | 0 | 0 | 19 | 19 | 19 | 19 | 19 | 19 |
| [P] 15 | 38 | 38 | 0 | 0 | 57 | 0 | 0 | 0 | 0 | 0 | 0 | 0 |
| [Q] 16 | 76 | 76 | 0 | 0 | 0 | 0 | 0 | 0 | 0 | 0 | 0 | 0 |
| [Y] 17 | 0 | 0 | 0 | 0 | 0 | 0 | 0 | 0 | 0 | 0 | 0 | 0 |
| [Z] 18 | 190 | 0 | 190 | 209 | 0 | 0 | 0 | 209 | 209 | 0 | 209 | 0 |

FIG. 7

| PATTERN CODE: | CURRENT STATE: | | | | | | | | | |
|---|---|---|---|---|---|---|---|---|---|---|
| | [RESET] 0 | [Y] 19 | [OQD] 38 | [P] 57 | [N1] 76 | [N2] 95 | [Y] 114 | [G1] 133 | [G2] 152 | [G3] 171 |
| [A] 0 | 114 | 0 | 0 | 114 | 0 | 0 | 0 | 0 | 0 | 0 |
| [B] 1 | 0 | 0 | 0 | 0 | 0 | 0 | 0 | 0 | 0 | 0 |
| [C] 2 | 0 | 0 | 0 | 0 | 0 | 0 | 0 | 0 | 0 | 0 |
| [D] 3 | 38 | 0 | 0 | 38 | 0 | 0 | 0 | 0 | 0 | 0 |
| [E] 4 | 0 | 0 | 0 | 0 | 0 | 0 | 0 | 0 | 0 | 0 |
| [F] 5 | 114 | 0 | 0 | 114 | 0 | 0 | 0 | 0 | 0 | 0 |
| [G] 6 | 133 | 133 | 133 | 133 | 0 | 0 | 0 | 152 | 171 | 0 |
| [H] 7 | 0 | 0 | 0 | 0 | 0 | 0 | 0 | 0 | 0 | 0 |
| [I] 8 | 0 | 0 | 0 | 0 | 0 | 0 | 0 | 0 | 0 | 0 |
| [J] 9 | 0 | 0 | 0 | 0 | 0 | 0 | 0 | 0 | 0 | 0 |
| [K] 10 | 0 | 0 | 0 | 0 | 0 | 0 | 0 | 0 | 0 | 0 |
| [L] 11 | 114 | 0 | 0 | 114 | 0 | 0 | 0 | 0 | 0 | 0 |
| [M] 12 | 114 | 0 | 0 | 114 | 0 | 0 | 0 | 0 | 0 | 0 |
| [N] 13 | 76 | 76 | 76 | 76 | 95 | 0 | 0 | 76 | 76 | 76 |
| [O] 14 | 38 | 38 | 0 | 38 | 38 | 0 | 38 | 38 | 0 | 0 |
| [P] 15 | 57 | 57 | 57 | 0 | 0 | 0 | 0 | 57 | 57 | 57 |
| [Q] 16 | 38 | 38 | 38 | 0 | 0 | 0 | 0 | 38 | 38 | 38 |
| [Y] 17 | 19 | 19 | 19 | 19 | 19 | 19 | 0 | 19 | 19 | 19 |
| [Z] 18 | 0 | 0 | 0 | 0 | 0 | 0 | 0 | 0 | 0 | 0 |

FIG. 8

| PATTERN CODE: | CURRENT STATE: | |
|---|---|---|
| | [RESET] 0 | [QY] 19 |
| [A] 0 | 0 | 0 |
| [B] 1 | 0 | 0 |
| [C] 2 | 0 | 0 |
| [D] 3 | 0 | 0 |
| [E] 4 | 0 | 0 |
| [F] 5 | 0 | 0 |
| [G] 6 | 0 | 0 |
| [H] 7 | 0 | 0 |
| [I] 8 | 0 | 0 |
| [J] 9 | 0 | 0 |
| [K] 10 | 0 | 0 |
| [L] 11 | 0 | 0 |
| [M] 12 | 0 | 0 |
| [N] 13 | 0 | 0 |
| [O] 14 | 0 | 0 |
| [P] 15 | 0 | 0 |
| [Q] 16 | 19 | 19 |
| [Y] 17 | 19 | 19 |
| [Z] 18 | 0 | 0 |

FIG. 9

| PATTERN CODE: | CURRENT STATE: | | | | | | |
|---|---|---|---|---|---|---|---|
| | [RESET] 0 | [FG] 19 | [O] 38 | [H1] 57 | [H2] 76 | [J] 95 | [N] 114 |
| [A] 0 | 0 | 0 | 0 | 0 | 0 | 0 | 0 |
| [B] 1 | 0 | 0 | 0 | 0 | 0 | 0 | 0 |
| [C] 2 | 0 | 0 | 0 | 0 | 0 | 0 | 0 |
| [D] 3 | 0 | 0 | 0 | 0 | 0 | 0 | 0 |
| [E] 4 | 0 | 0 | 0 | 0 | 0 | 0 | 0 |
| [F] 5 | 19 | 19 | 0 | 0 | 0 | 19 | 0 |
| [G] 6 | 19 | 19 | 0 | 0 | 0 | 19 | 0 |
| [H] 7 | 57 | 0 | 57 | 0 | 0 | 0 | 76 |
| [I] 8 | 114 | 0 | 0 | 114 | 0 | 0 | 0 |
| [J] 9 | 95 | 0 | 0 | 95 | 95 | 0 | 0 |
| [K] 10 | 0 | 0 | 0 | 0 | 0 | 0 | 0 |
| [L] 11 | 0 | 0 | 0 | 0 | 0 | 0 | 0 |
| [M] 12 | 0 | 0 | 0 | 0 | 0 | 0 | 0 |
| [N] 13 | 0 | 0 | 0 | 0 | 0 | 0 | 0 |
| [O] 14 | 38 | 38 | 0 | 0 | 0 | 0 | 0 |
| [P] 15 | 0 | 0 | 0 | 0 | 0 | 0 | 0 |
| [Q] 16 | 0 | 0 | 0 | 0 | 0 | 0 | 0 |
| [Y] 17 | 0 | 0 | 0 | 0 | 0 | 0 | 0 |
| [Z] 18 | 0 | 0 | 0 | 0 | 0 | 0 | 0 |

FIG. 10

PRIORITIZED RULE BASED APPARATUS FOR DIAGNOSIS AND TREATMENT OF ARRHYTHMIAS

This application is a division of application Ser. No. 08/874,067 filed Jun. 12, 1997 U.S. Pat. No. 5,855,593 which is a File Wrapper Continuation of Ser. No. 08/633,254 filed Jun. 19, 1996 abandoned, which is a continuation of Ser. No. 08/413,570 filed Mar. 30, 1995 issued Aug. 13, 1996 as U.S. Pat. No. 5,545,186.

BACKGROUND OF THE INVENTION

This invention relates to devices which detect and/or treat tachyarrhythmias (rapid heart rhythms), and more specifically, to mechanisms to distinguish among various tachyarrhythmias and to provide appropriate therapies to treat the identified tachyarrhythmias.

Early automatic tachyarrhythmia detection systems for automatic cardioverter/defibrillators relied upon the presence or absence of electrical and mechanical heart activity (such as intra-myocardial pressure, blood pressure, impedance, stroke volume or heart movement) and/or the rate of the electrocardiogram to detect hemodynamically compromising ventricular tachycardia or fibrillation.

In pacemaker/cardioverter/defibrillators presently in commercial distribution or clinical evaluation fibrillation is generally distinguished from ventricular tachycardia using ventricular rate based criteria, In such devices, it is common co specify the rate or interval ranges that characterize a tachyarrhythmia as opposed to fibrillation. However, some patients may suffer from ventricular tachycardia and ventricular fibrillation which have similar or overlapping rates, making it difficult to distinguish low rate fibrillation from high rate tachycardia. In addition, ventricular fibrillation may display R—R intervals which vary considerably, resulting in intervals that may fall within both the tachycardia and fibrillation rate or interval ranges, or outside both. Similarly, supraventricular arrhythmias may be the cause of high ventricular rates, or may be present during ventricular arrhythmias, further increasing the possibilities of misdiagnosis.

Presently available pacemaker/cardioverter/defibrillator arrhythmia control devices such as the Model 7219 and Model 7217 devices commercially available from Medtronic, Inc., employ programmable fibrillation interval ranges and tachycardia detection interval ranges, along with measurement of suddenness of onset and rate variability. For future generations of devices, numerous detection and classification systems have been proposed. Numerous patents, including U.S. Pat. No. 5,217,021 issued to Steinhaus et al., U.S. Pat. No. 5,086,772 issued to Larnard et al., U.S. Pat. No. 5,058,599 issued to Andersen and U.S. Pat. No. 5,312,441 issued to Mader et al propose waveform morphology analysis systems for determining the type and origin of detected arrhythmias. Other patents, including U.S. Pat. No. 5,205,583 issued to Olson, U.S. Pat. No. 5,913,550 issued to Duffin, U.S. Pat. No. 5,193,535 issued to Bardy et al., U.S. Pat. No. 5,161,527 issued to Nappholz et al., U.S. Pat. No. 5,107,850 issued to Olive and U.S. Pat. No. 5,048,521, issued to Pless et al. propose systems for analysis of order and timing of atrial and ventricular events.

In the existing and proposed devices discussed above, one or two basic strategies are generally followed. A first strategy is to identify heart events, event intervals or event rates as they occur as indicative of the likelihood of the occurrence of specific types of arrhythmias, with each arrhythmia having a preset group of criteria which must be met as precedent to detection or classification. As events progress, the criteria for identifying the various arrhythmias are all monitored simultaneously, with the first set of criteria to be met resulting in detection and diagnosis of the arrhythrnia. A second strategy is to define a set of criteria for events, event intervals and event rates which is generally indicative of a group of arrhythmias, and following those criteria being met, analyzing preceding or subsequent events to determine which specific arrhythmia is present. In the Medtronic Model 7219 devices, an arrhythmia detection and classification system generally as disclosed in U.S. Pat. No. 5,342,402, issued to Olson et al., incorporated herein by reference in its entirety, is employed, which uses both strategies together.

SUMMARY OF THE INVENTION

The arrhythmia detection and classification system of the present invention employs a prioritized set of inter-related rules for arrhythmia detection. Each rule contains a set of one or more "clauses" which must be satisfied (criteria which must be met). While all clauses of a rule are satisfied, the rule is indicated to be met. In the context of the present application this is referred to as the rule "firing". It is possible for multiple rules to be "firing" at the same time, with the highest priority rule taking precedence. Some rules trigger delivery of therapy when firing. Other rules inhibit delivery of therapy when firing. The highest priority rule firing at any specific time controls the behavior of the device. For example, the firing of a rule which triggers therapy is superseded by the firing of higher priority rules preventing delivery of therapy. Rules cease firing when their clauses cease to be satisfied, whether or not a therapy is triggered by the rule.

Each rule includes a set of clauses which, when satisfied, indicate the likely occurrence of a specified type of heart rhythm, including various tachyarrhythmias, sinus tachycardia and normal sinus rhythm. A specific rhythm or tachyarrhythmia may have more than one associated rule. The rules are interrelated, such that progress toward meeting the requirements of a clause of one rule may also be the subject matter of a clause of a different rule.

The specific criteria set forth by the clauses of the various rules as disclosed include a number of known criteria for evaluating heart rhythm, including the entire arrhythmia detection and classification system employed in the presently available Medtronic 7219 pacemaker cardioverter defibrillators, as well as criteria disclosed in U.S. Pat. No. 5,330,508, issued to Gunderson, as will be discussed below. In addition, a number of new evaluation criteria are included within the clauses of various rules. One such new detection methodology is based upon the classification of the events occurring associated with the sequence of two ventricular depolarizations into a limited number of event patterns, based upon the number and times of occurrences of atrial events, preceding the two most recent ventricular events. An event pattern is developed for each individual ventricular event, so that successive event patterns overlap one another. The inventors have determined that certain sequences of event patterns are strongly indicative of specific types of heart rhythms. For heart rhythms of which this is true, a defined set of indicative event pattern sequences or a "grammar" is defined. Adherence of the heart rhythm to the grammars associated with various heart rhythms is determined by simultaneously operating continuous recognition machines, the outputs of which form the subject matter of one or more clauses, within the hierarchy of rules.

An additional new classification criteria included in some rules is a measure of the co-variance of the R wave to P wave interval with the R wave to R wave interval, which is employed as an index of the likelihood that the depolarizations of the ventricles over a preceding series of events have had an atrial origin. This criterion is applied in conjunction with rules intended to identify the likely occurrence of atrial fibrillation and atrial flutter.

An additional new classification criterion comprises a methodology of identifying the likelihood that events sensed in the atrium are in fact far field R waves, rather than P waves. The occurrence of such identified far field R waves over a sequence of R—R intervals is employed in conjunction with rules indicative of various types of supraventricular tachycardias.

BRIEF DESCRIPTION OF THE DRAWINGS

FIG. 5 is a table illustrating the operation of a continuous recognition machine employed by a preferred embodiment of the present invention to accomplish classification of heart event sequences according to the system illustrated in FIG. 4.

FIG. 6 is a table illustrating the operation of a continuous recognition machine employed by a preferred embodiment of the present invention to identify the probable occurrence of normal sinus rhythm or sinus tachycardia based upon series of heart event sequences as classified using the continuous recognition machine illustrated in FIG. 5.

FIG. 7 is a table illustrating the operation of a continuous recognition machine employed by a preferred embodiment of the present invention to identify the probable occurrence of simultaneous ventricular and supraventricular tachycardias based upon series of heart event sequences as classified using the continuous recognition machine illustrated in FIG. 5.

FIG. 8 is a table illustrating the operation of a first continuous recognition machine employed by a preferred embodiment of the present invention to identify the probable occurrence of atrial fibrillation or flutter based upon series of heart event sequences as classified using the continuous recognition machine illustrated in FIG. 5.

FIG. 9 is a table illustrating the operation of a second continuous recognition machine employed by a preferred embodiment of the present invention to identify the probable occurrence of atrial fibrillation or flutter based upon series of heart event sequences as classified using the continuous recognition machine illustrated in FIG. 5.

FIG. 10 is a table illustrating the operation of a continuous recognition machine employed by a preferred embodiment of the present invention to identify the probable occurrence of AV nodal tachycardia based upon series of heart event sequences as classified using the continuous recognition machine illustrated in FIG. 5.

DETAILED DESCRIPTION OF THE PREFERRED EMBODIMENTS

Figure 1:
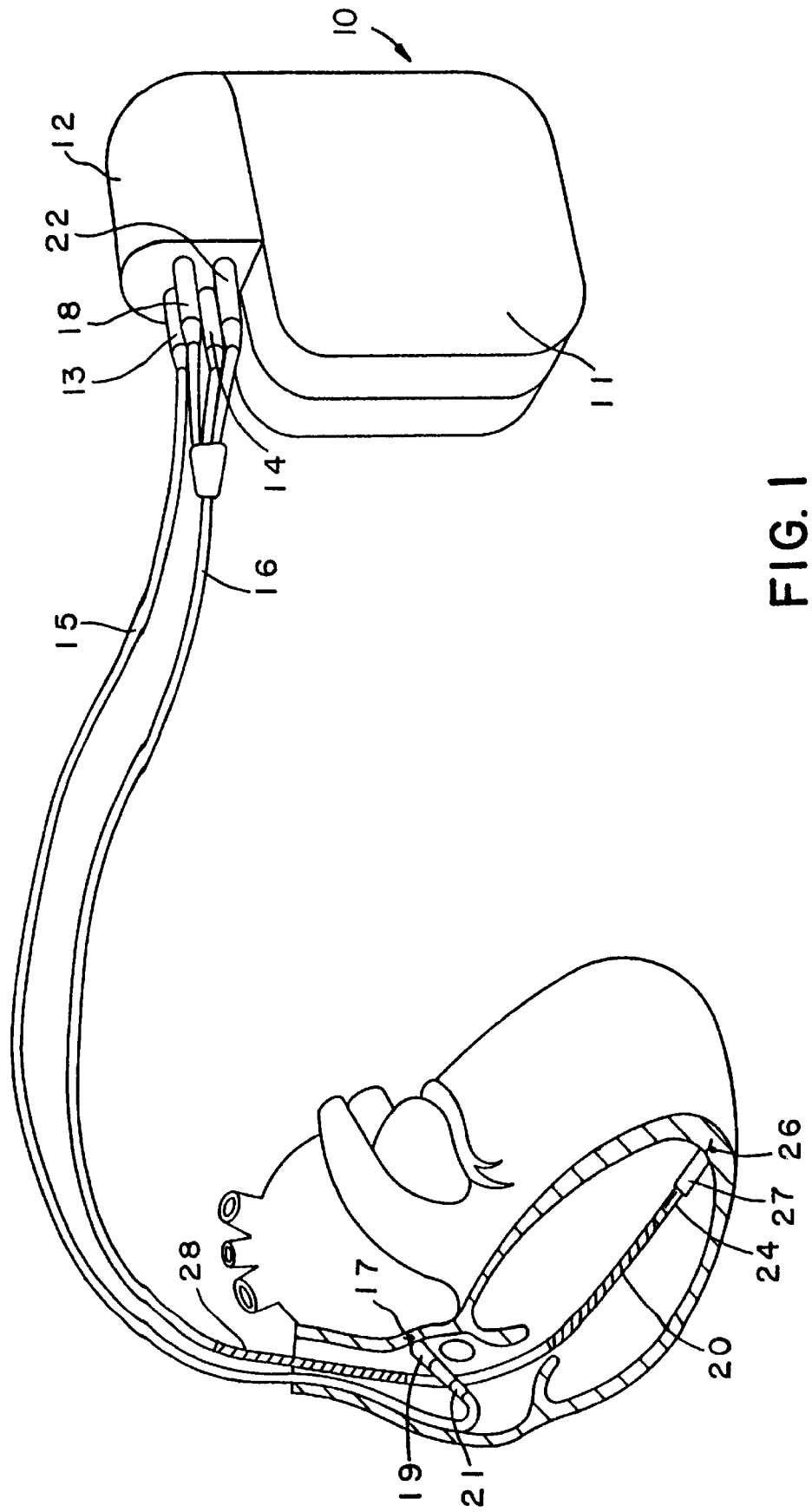
FIG. 1 illustrates a first embodiment of an implantable pacemaker/cardioverter/defibrillator of a type appropriate for use in practicing the present invention, in conjunction with a human heart.

FIG. 1 illustrates a pacemaker/cardioverter/defibrillator 10 and lead set according to the present invention. The ventricular lead includes an elongated insulative lead body 16, carrying four mutually insulated conductors. Located on the lead body are a ring electrode 24, an extendable helix electrode 26, mounted retractably within an insulative electrode head 27, and elongated coil electrodes 20 and 28. Each of the electrodes is coupled to one of the coiled conductors within the lead body 16. Electrodes 24 and 26 are employed for cardiac pacing and for sensing ventricular depolarizations. Electrodes 20 and 28 are employed in conjunction with the conductive housing 11 of the pacemaker/cardioverter/defibrillator 10 for delivery of ventricular cardioversion and defibrillation pulses. At the proximal end of the lead body 16 are two unipolar connectors 18 and 22 which each carry a connector pin coupled to one of the coiled electrodes 20 and 28. Electrical connector 14 is an in-line bipolar connector carrying a connector ring and a connector pin, coupled to electrodes 24 and 26, respectively.

The atrial lead as illustrated is a conventional bipolar atrial pacing lead. The atrial lead includes an elongated insulative lead body 15, carrying two concentric coiled conductors, separated from one another by tubular insulative sheaths. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. At the proximal end of the lead is an in-line connector 13 which carries a connector ring and a connector pin, coupled to electrodes 21 and 17, respectively. In alternative lead systems, a defibrillation electrode, for example corresponding to electrode 28, might instead be mounted to the atrial lead, or might be mounted to a coronary sinus lead, for location in the coronary sinus and great cardiac vein.

An implantable pacemaker/cardioverter/defibrillator 10 is shown in combination with the leads, with the lead connectors 13, 14, 18 and 22 inserted into the connector block 12, which contains corresponding electrical connectors for coupling to the various connector rings and pins. Optionally, insulation of the outward facing portion of the housing 11 of the pacemaker/cardioverter/defibrillator 10 may be provided in the form of a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 serves as a subcutaneous defibrillation electrode, used in conjunction with one or both of electrodes 20 and 28.

Figure 2:
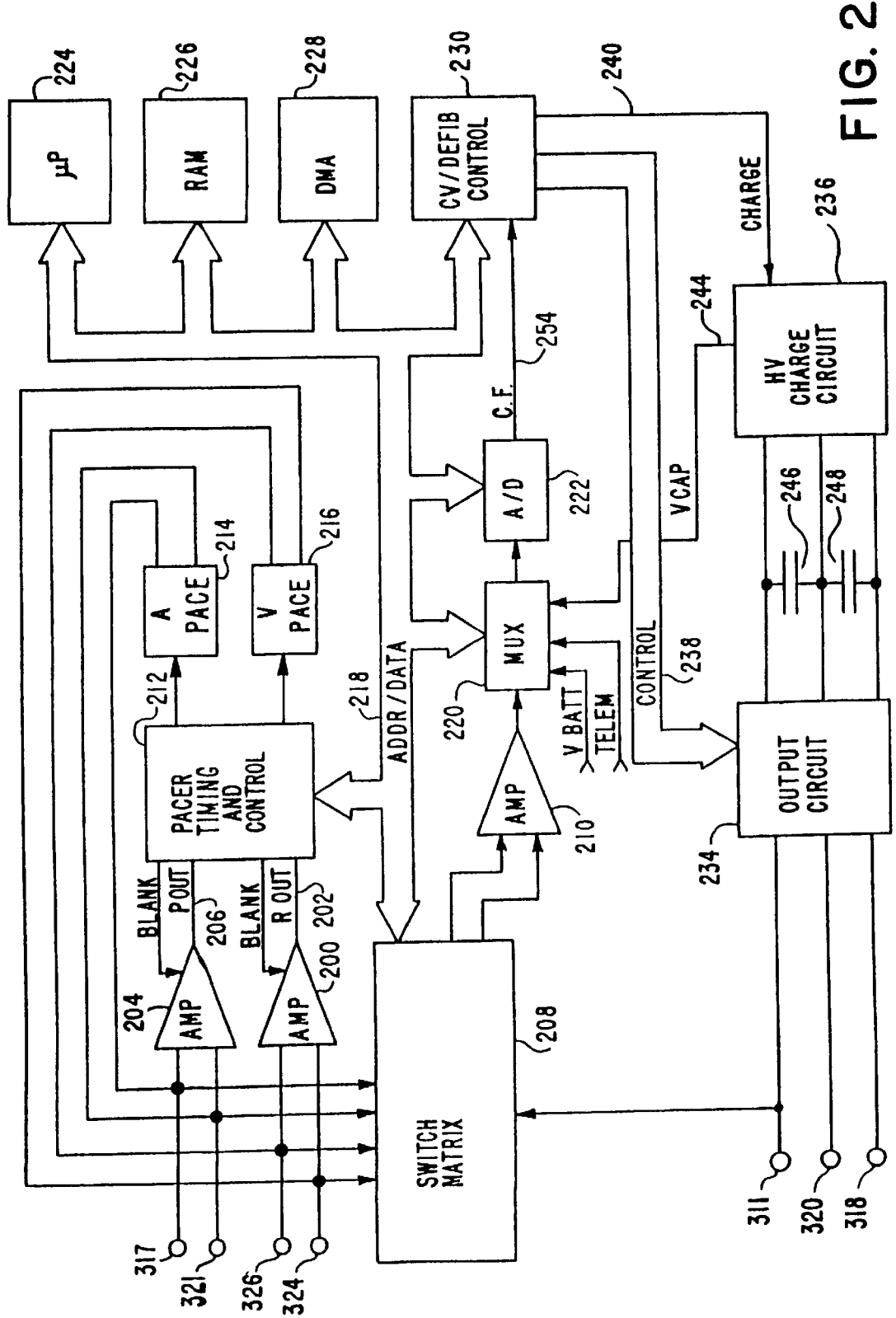
FIG. 2 illustrates a functional schematic diagram of an implantable pacemaker/cardioverter/defibrillator in which the invention may be practiced.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implant able pacemaker/cardioverter/defibrillator. Electrode 320 corresponds to electrode 20 and is a defibrillation electrode located in the right ventricle. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 311, 318 and 320 are coupled to high voltage output circuit 234. Electrodes 324 and 326 are located on or in the ventricle and are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art.

Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on timeout trigger generation of pacing pulses by pacer output circuitry 214 and 216, which are coupled to electrodes 317, 321, 324 and 326. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R—R intervals, P—P intervals, P-R intervals and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. A portion of the memory 226 (FIG. 4) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present invention may include prior art tachyarrhythmia detection algorithms. As described below, the entire ventricular arrhythmia detection methodology of presently available Medtronic pacemaker/cardioverter/defibrillators is employed as part of the arrhythmia detection and classification method according to the disclosed preferred embodiment of the invention. However, any of the various arrhythmia detection methodologies known to the art, as discussed in the Background of the Invention section above might also usefully be employed in alternative embodiments of the invention.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 7,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. If atrial defibrillation capabilities are included in the device, appropriate systems for delivery and synchronization of atrial cardioversion and defibrillation pulses and for controlling the timing functions related to them may be found in PCT Pat. Application No. WO92/18198 by Adams et al., published Oct. 29, 1992, and in U.S. Pat. No. 4,316,472 by Mirowski et al., issued Feb. 23, 1982, both incorporated herein by reference in their entireties.

However, any known cardioversion or defibrillation pulse control circuitry is believed usable in conjunction with the present invention. For example. circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implant able cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may abe scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that fibrillation is identified, the typical therapy will be delivery of a high amplitude defibrillation pulse, typically in excess of 5 joules. Lower energy levels may be employed for cardioversion. As in the case of currently available implant able pacemakers/cardioverter/ defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 3:
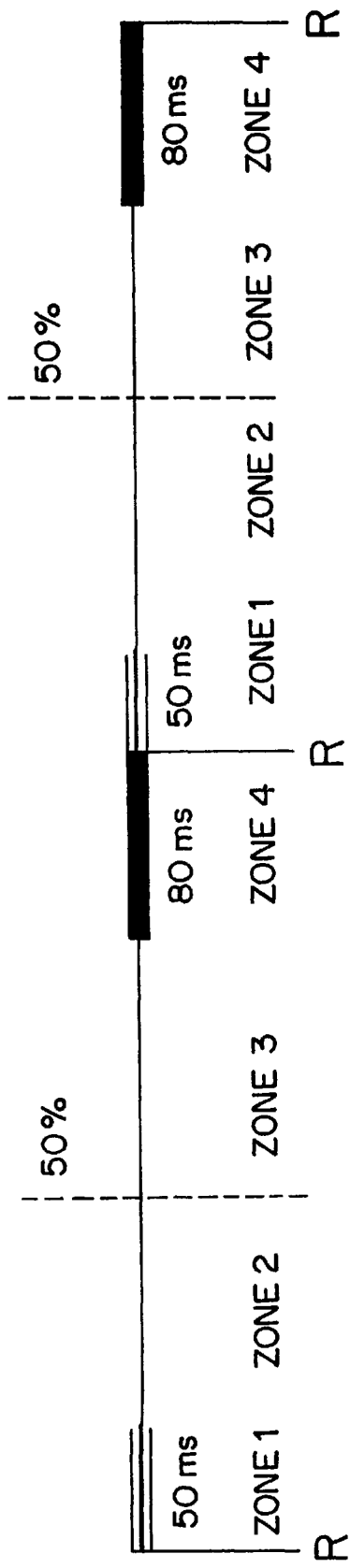
FIG. 3 illustrates the basic timing intervals employed by a preferred embodiment of the present invention to classify sequences of heart events.

As noted above, with each ventricular event, the timing of atrial and ventricular events occurring during the preceding two R—R intervals is analyzed to develop a "pattern code". FIG. 3 illustrates the various defined time intervals, employed to develop the pattern codes. Each of the two R—R intervals is divided into four zones, in which zone 1 encompasses the first 50 milliseconds following the ventricular event initiating the R—R interval, zone 2 extends from the end of zone 1 until halfway through the R—R interval. Zone 3 extends from halfway through the R—R interval to 80 milliseconds prior to the ventricular event ending the R—R interval and zone 4 includes the last 80 milliseconds of the R—R interval.

In order to determine the pattern codes, each individual R—R interval is assigned a "beat code", based on the number of occurrence of atrial events during the R—R interval, and their location with regard to the four defined zones. Three criteria are evaluated in order to assign each R—R interval with a beat code, including the number of atrial events occurring the R—R interval, referred to as the "P count", the duration of the R-P interval associated with the R—R interval, and the duration of the P-R interval associated with the R—R interval. The R-P interval is the time in milliseconds from the beginning ventricular event in the R—R interval to the first atrial event occurring within the interval, if any. The P-R interval is the time in milliseconds from the last atrial event in the R—R interval, if any, to the concluding ventricular event in the R—R interval. It should be noted that if multiple atrial events occur during the R—R interval, the sum of the R-P and P-R intervals will not equal the R—R interval. Based on the P count and the times of occurrence of the atrial depolarizations, a beat count of zero to nine is generated. The algorithm for generating the beat code is as follows.

If P count equals 1 and an atrial event occurs in zone 3, the beat code is zero. If P count equals 1 and the atrial event occurs in zone 1, the beat code is 1. If P count equals 1 and the atrial event occurs in zone 4, the beat code is 2. If P count equals 1 and the atrial event occurs in zone 2, the beat code is 3.

If P count equals 2, and an atrial event occurs in zone 3 but not zone 1, the beat code is 9. If P count equals 2 and an atrial event occurs in zone and in zone 1, the beat code is 4. If P count equals 2 and atrial events occur in zones 1 and 4, the beat code is 5. All other R—R intervals containing two atrial events result in a beat code of 6.

If P count is greater than or equal to 3, the beat code is 8. If P count is equal to 0, the beat code is 7.

Figure 4:
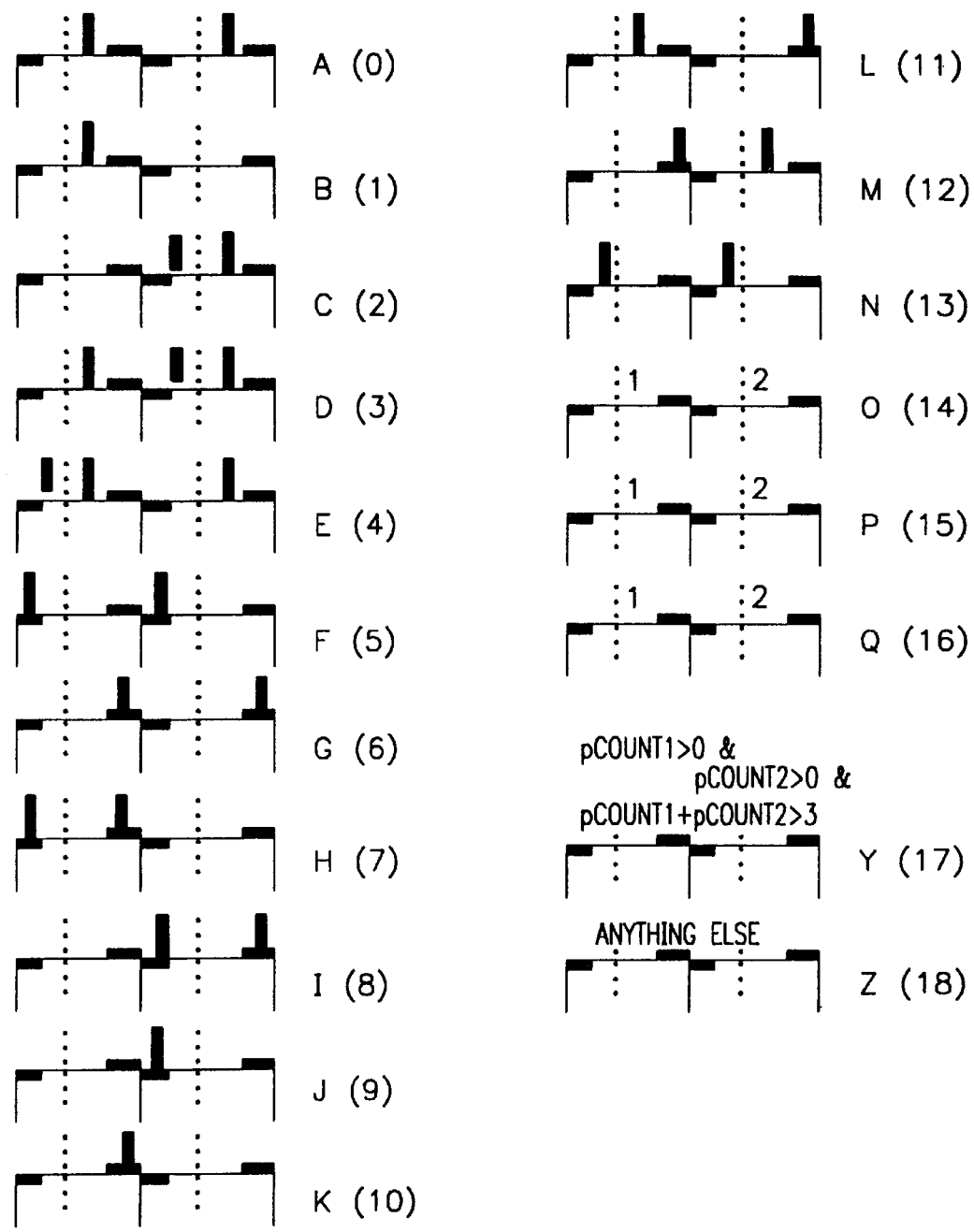
FIG. 4 illustrates the classification system employed by a preferred embodiment of the present invention to classify sequences of heart events.

Given 10 beat codes, it would be expected that 100 corresponding pattern codes for two R—R interval sequences would be generated. However, the inventors have determined that the library of event patterns may usefully be reduced substantially, and have derived a set of 18 pattern codes as illustrated in FIG. 4. In the illustrations, two successive R—R intervals are illustrated, with downward extending lines indicative of ventricular events and upward extending lines indicative of atrial events. Zone 1 is illustrated as a short horizontal bar extending from the first ventricular event in each R—R interval. Zone 4 is illustrated as a short horizontal bar extending back from the last ventricular event in each R—R interval. A vertically extending dotted line is indicative of the dividing line between zone 2 and zone 3, halfway through the R—R interval, upwardly extending lines, coupled to the horizontal base line are indicative of atrial events occurring in the specific zone illustrated. Upwardly extending lines which float above the base line are indicative of atrial events that may occur in either of the two zones to which they are adjacent.

Pattern code A. corresponding to a beat code pair (0,0) is a pattern code likely to be seen with high frequency in sinus rhythms, including normal sinus rhythm and sinus tachycardia.

Pattern code B, corresponding to beat code (0,7) arises, among other times, when a premature ventricular contraction occurs and is detected prior to the next atrial depolarization.

Pattern code C corresponds to beat code pairs (7,4) or (7,9), and arises, among other times, in the aftermath of isolated PVC's.

Pattern code D, corresponding to beat code pairs (0,9) arises, among other times, when an isolated premature atrial contraction occurs, with no corresponding ventricular event.

Pattern code E, corresponding to beat code (9,0) arises, among other times, in the aftermath of an isolated PAC, with resumption of normal sinus rhythm.

Pattern code F, corresponding to beat code pair (1,1) arises, among other times, during a junctional rhythm, with the atrial depolarizations being detected closely following depolarizations in the ventricles. It also arises in disassociated rhythms in which the atria and ventricles beat independently, but slightly out of phase.

Pattern code G, corresponding to beat code pair (2,2) arises, among other times, when a rhythm has a junctional origin, with ventricular depolarizations detected just slightly after atrial depolarizations. It also arises in disassociated rhythms in which atria and ventricle beat independently at close to the same rate, but slightly out of phase.

Pattern code H, corresponding to beat code pair (5,7) arises, among other times, in junctional rhythms in which atrial and ventricular depolarizations are sensed closely spaced to one another, but in no consistent time order.

Pattern code I, corresponding to beat code pair (7,5) and pattern code J, corresponding to beat code pair (7,1) are both employed for recognition of AV nodal reentrant tachycardia.

Pattern code K, corresponding to beat code pair (2,7) arises, among other times during nodal rhythms, as well as ventricular tachycardia, ventricular fibrillation and ventricular flutter, but rarely, if at all, occurs in cases of atrial fibrillation.

Pattern code L, corresponding to beat code (0,2) occasionally arises in cases of dual tachycardia, in which the atria and ventricles are beating independently, but out of phase. Pattern code M, beat code pair (2,0) also arises in these situations.

Pattern code N, corresponding to beat code pair (3,3) arises in cases of ventricular tachycardia with one to one retrograde conduction.

Pattern code O is a default pattern code, based on the failure of the pattern code to correspond to any of codes A-N, above, with the additional requirement that the P count for the first R—R interval is 1 and the P count for the second R—R interval is 2. This pattern code arises frequently in atrial fibrillation, among other rapid atrial rhythms. Pattern code P is also a default pattern code, designated if the beat code pair does not correspond to any of the beat code pairs designated in conjunction with pattern codes A-N, above, with a P count for the first R—R interval of 2 and a P count for the second R—R interval of 1.

Pattern code Q is a default pattern code assigned in response to beat code pairs which do not correspond to any of pattern codes A-N above, in which both P counts are 2. Like pattern codes O and P, this pattern code is indicative of atrial fibrillation, and/or rapid atrial rhythms.

Pattern Code Y is a default pattern code assigned to all beat code pairs not falling into any of previously defined pattern codes A-Q, in which there is at least one atrial event in each R—R interval, and the sum of the two P counts exceeds 3. Pattern code Z is a default pattern code assigned to all beat code pairs not corresponding to any of pattern codes A-Y above.

While the above rules appear to be complex, they may be very conveniently implemented by means of a look up table, as set forth in FIG. 5, which assigns each of the 100 possible beat code pairs to one of the designated pattern codes. By use of the look up table stored in memory, the microprocessor within the device can readily and rapidly determine the appropriate pattern code associated with each successive ventricular event. These pattern codes can be stored as numbers, as indicated in brackets, and their order analyzed by means of a software implemented continuous recognition machine to determine whether the sequences of pattern codes correspond to defined grammars corresponding to specific arrhythmias or groups of arrhythmias. The operation of the continuous recognition machines in order to accomplish this result is discussed in more detail, below. However, for purposes of understanding the general operation of the device, in conjunction with the functional flowcharts of FIG. 11, it need only be understood that the continuous recognition machines output a count indicative of the degree of correspondence of the sensed rhythm to the defined grammars for each arrhythmia, and that the rules for identifying the various arrhythmias include clauses setting forth criteria against which the output counts of the continuous recognition machines are compared.

FIG. 6 illustrates the look-up table employed in conjunction with the continuous recognition machine for recognizing pattern code sequences corresponding to normal sinus rhythm or to sinus tachycardia. The continuous recognition machine is implemented by the microprocessor applying the pattern codes, as they are generated with each ventricular event, to the look-up table. The table defines a set of sequential states, beginning with the reset state 0, and a set of other defined states, arranged horizontally across the table. Possible pattern codes are listed vertically. In operation, with each ventricular event, the processor determines its present state and the most recent pattern code. Based on the table, the processor transitions to the next state, and awaits the next pattern code. As long as the pattern codes adhere to the defined grammar for the rhythm in question, the reset state is avoided. Adherence to the defined grammar over an extended sequence of beats is determined by means of a corresponding count, which may be incremented with each pattern code adhering to the grammar, and may be reset to zero or decremented in response to pattern codes which do not adhere to the grammar as indicated by a return to the reset state. The current count for each continuous recognition machine is compared against a defined threshold value in one or more clauses, in one or more rules.

The continuous recognition machine for recognition of normal sinus rhythm requires strict adherence to the grammar defined by the look-up table. This type of continuous recognition machine is referred to herein as a "CRM". A stored count CRMST is incremented, up to its associated threshold value, in response to each transition to a non-reset state (or in response to the first R—R interval after a power-on reset or other device reset, where the pattern code is unknown). The CRMST count is reset to zero with each failure to adhere to the grammnar. The other CRM's in the device work the same way. The value of CRMST is employed in clauses of rules for recognizing normal sinus rhythm and ventricular tachycardia.

The continuous recognition machine for recognition of sinus tachycardia employs the same look-up table, but requires a less strict adherence to the grammar. This type of pattern recognition machine is referred to herein as a continuous recognition machine with exponential decay or "CRMed". The CRMed for sinus tachycardia employs a count, "CRMedST" which is incremented, up to a count of 13, in response to each transition to a non-reset state (or in response to the first R—R interval after a power-on reset or other device reset, where the pattern code is unknown). If CRMedST is less than 8, the count is reset to zero on a failure to adhere to the grammar. If the count is 8 or more, a failure to adhere to the grammar causes a decrement of 1, with exponentially increasing decrements of 2, 4 and 8 with each additional, successive failure. Thus, if the count is at 14, four successive failures to meet the grammar will result in reset, with shorter sequences of failures to adhere to the grammar causing resets at lower counts. The various other CRMed's in the device work the came way. On each ventricular event, all CRM and CRMed counts are updated by the processor and compared against applicable recognition threshold values. The value of CRMedST is compared to its corresponding threshold value in a clause of the rule for recognizing sinus tachycardia.

FIG. 7 is a look-up table employed by the CRMed used to detect the likely occurrence of simultaneous ventricular and supraventricular tachyarrhythmias. The Count associated with the CRMed is designated "CRMedDT". The value of CRMedDT is employed in clauses of rules for recognizing simultaneous ventricular and supraventricular tachycardias and for identifying atrial fibrillation or flutter.

FIG. 8 is a look-up table employed by the CRMed used to detect the likely occurrence of atrial fibrillation or flutter. The Count associated with the CRMed is designated "CRMedAF". The value of CRMedAF is employed in a clause of the rule for recognizing simultaneous ventricular and supraventricular tachycardias.

FIG. 9 is a look-up table employed by the CRM used to detect the likely occurrence of atrial fibrillation or flutter. The Count associated with the CRMED is designated "CRMAL". The value of CRMAL is employed in a clause of a rule for recognizing atrial fibrillation or flutter.

FIG. 10 is a look-up table employed by the CRM used to detect the likely occurrence of atrial-ventricular nodal tachycardia. The Count associated with the CRM is designated "CRMAVNT". The value of CRMAVNT is employed in a clause of a rule for recognizing AV nodal reentrant tachycardia.

In addition to adherence to the defined grammars as set forth above, the rules of the present invention also employ all of the various rate and interval based recognition criteria presently employed by the Medtronic Model 7219 implantable pacemaker/cardioverter/defibrillator. These criteria are discussed in detail in U.S. Pat. No. 5,342,402, issued to Olson, incorporated herein by reference in its entirety. These criteria are also discussed below.

Presently available pacemaker-cardioverter-defibrillator devices, such as the Model 7219 PCD devices available from Medtronic, Inc., employ programmable fibrillation interval ranges and tachycardia detection interval ranges. In these devices, the interval range designated as indicative of fibrillation consists of intervals less than a programmable interval (FDI) and the interval range designated as indicative of ventricular tachycardia consists of intervals less than a programmable interval (TDI) and greater than or equal to FDI. R—R intervals falling within these ranges are measured and counted to provide a count (VTEC) of R—R intervals falling within the ventricular tachycardia interval range and a count (VFEC) of the number intervals, out of a preceding series of a predetermined number (FEB) of intervals, which fall within the ventricular fibrillation interval range. VTEC is incremented in response to R—R intervals that are greater than or equal to FDI but shorter than TDI, is reset to zero in response to intervals greater than or equal to TDI and is insensitive to intervals less than FDI. VTEC is compared to a programmed value (VTNID) and VFEC is compared to a corresponding programmable value (VFNID). When one of the counts equals its corresponding programmable value, the device diagnoses the presence of the corresponding arrhythmia, i.e. tachycardia or fibrillation and delivers an appropriate therapy, e.g. anti-tachycardia pacing, a cardioversion pulse or a defibrillation pulse. In addition, the physician may optionally require that the measured R—R intervals meet a rapid onset criterion before VTEC can be incremented and can also optionally require that should a rate stability criterion fail to be met, VTEC will be reset to zero. If the device is further programmed to identify the occurrence of a fast ventricular tachycardia, detection of ventricular fibrillation or tachycardia according to the above method serves as a provisional detection, which may be modified, as discussed below.

In addition to the tachycardia and fibrillation detection criteria (VTEC>=VTNID, VFEC>=VFNID) discussed above, detection of tachycardia or fibrillation detection may also be accomplished using a combined count of all intervals indicative of tachycardia or fibrillation. This combined count (VFEC+VTEC) is compared to a combined count threshold (CNID). If VTEC+VFEC is equal or greater than CNID, the device checks to see whether VFEC is at least a predetermined number (e.g. 6). If so, the device checks to determine how many of a number (e.g. 8) of the immediately preceding intervals are greater or equal to FDI. If a predetermined number (e.g. 8) are greater than or equal to FDI, tachycardia is detected, otherwise ventricular fibrillation is detected. If the device is further programmed to identify the occurrence of a fast ventricular tachycardia, detection of ventricular fibrillation or tachycardia according to the above method serves as a provisional detection, which may be modified, as discussed below.

In addition, the device is provided with a method of distinguishing a fast ventricular tachycardia from either ventricular fibrillation or slow ventricular tachycardia. In conjunction with fast ventricular tachycardia detection, the physician determines whether detection of a fast ventricular tachycardia is to be accomplished following a provisional diagnosis of ventricular tachycardia, following a provisional diagnosis of ventricular fibrillation, or following either. If detection of fast ventricular tachycardia is enabled, then following provisional detection of ventricular tachycardia or fibrillation, as discussed above, the immediately preceding measured intervals are examined to determine whether the provisional detection of fibrillation or tachycardia should be confirmed or amended to indicate detection of fast ventricular tachycardia.

If fast ventricular tachycardia detection following a provisional detection of ventricular tachycardia is enabled, a value $FTDI_{max}$ is defined, which is greater than or equal to FDI. If fast ventricular tachycardia detection following a provisional detection of ventricular fibrillation is enabled, a value $FTDI_{min}$ is defined, which is less than or equal to FDI. If ventricular tachycardia is provisionally detected, intervals less than $FTDI_{max}$ are taken as indicative of fast ventricular tachycardia. If ventricular fibrillation is provisionally detected. intervals greater than or equal to $FTDI_{min}$ are taken as indicative of fast ventricular tachycardia.

If fibrillation was provisionally detected, the device may require that at least 7 or all 8 of the preceding 8 intervals fall within the fast ventricular tachycardia interval range (greater than or equal to $FTDI_{min}$) to detect fast ventricular tachycardia. Otherwise, the provisional detection of ventricular fibrillation is confirmed. If ventricular tachycardia is provisionally detected, the device may only require that at least 1 or 2 of the preceding 8 intervals fall within the fast ventricular tachycardia interval range (less than $FTDI_{max}$) in order to detect fast ventricular tachycardia. Otherwise, the provisional detection of (slow) ventricular tachycardia is confirmed.

The entire arrhythmia detection methodology of the Model 7219 is retained in the disclosed embodiment of the present invention. The criteria for detection of ventricular fibrillation, fast ventricular tachycardia and ventricular tachycardia according to this methodology comprise the three lowest priority rules employed for arrhythmia detection and classification.

The arrhythmia detection and classification scheme of the present invention also employs a measurement of R—R interval variability, as disclosed in U.S. Pat. No. 5,330,508, issued to Gunderson and incorporated herein by reference in its entirety. R—R interval variability is measured by sorting the 18 previous measured R—R intervals into bins, each bin being 10 ms in width, spanning the range of 240 ms through 2019 ms. The sum (RR Modesum) of the numbers of intervals in the two bins individually having the highest numbers of intervals is calculated and compared against preset threshold values. The higher the value of RR Modesum, the lower the variability of RR intervals, and the more likely the rhythm is a monomorphic ventricular tachycardia. The RR Modesum is compared against various threshold values in clauses of rules for detecting ventricular tachycardia, ventricular tachycardia in the presence of supraventricular tachycardia, atrial fibrillation or flutter, and AV nodal reentrant tachycardia. If, as following initialization or power on reset, 18 intervals have not been measured, the value of RR Modesum is defined as "unknown".

In conjunction with the operation of rules intended to identify the likely occurrence of ventricular and supraventricular tachycardia, the microprocessor also keeps track of the number of R—R intervals which likely contain sensed atrial events caused by farfield R-waves, out of a preceding series of R—R intervals. The microprocessor determines that an event sensed in the atrium is likely a farfield R-wave, according to the following methodology.

In response to the occurrence of R—R interval having a P count equal to 2, the R-P and P-R intervals for the R—R interval are compared to fixed thresholds. For example, the processor may check to determine whether the PR interval is less than or equal to 50 milliseconds or whether the R-P interval is less than or equal to 150 milliseconds. It should be kept in mind that in conjunction with an R—R interval having a P count of 2, the R-P interval is measured between the ventricular event initiating the R—R interval and the first occurring atrial event and the P-R interval is measured between the second to occur atrial event and the ventricular event ending the R—R interval.

If the P-R interval is less than or equal to 50 milliseconds, the processor compares the P-R interval to the average duration (PRave) of the eight most recent P-R intervals which are also less than 50 milliseconds. If the absolute value of the difference between the P-R interval and this PRave is less than or equal to 20 milliseconds, the processor then subtracts the shortest PR interval ($PR_{min}$) out of the preceding eight PR intervals less than 50 milliseconds from the PR interval having the greatest duration ($PR_{max}$) out of the eight most recent intervals less than 50 milliseconds. If the difference between $P_{max}$ and $P_{min}$ is less than or equal to 30 milliseconds, the processor compares the P—P interval between the two atrial events during the R—R interval under consideration with the P—P interval separating the first atrial event in the R—R interval in consideration from the last atrial event in the proceeding R—R interval. If the difference between these two values is greater than or equal to 30 milliseconds, the processor determines that the R—R interval under consideration likely includes a farfield R-wave.

Similarly, if the measured R-P interval in the R—R interval under question is less than or equal to 150 milliseconds, the processor subtracts the average (RPave) of the eight most recent R-P intervals less than 150 milliseconds from the R-P interval in the RR interval under consideration. If the absolute value between the R-P interval and Rpave is less or equal to 20 milliseconds, the processor checks to determine whether the maximum R-P interval ($RP_{max}$) of the eight most recent RP intervals less than 150 milliseconds exceeds the minimum RP interval ($RP_{min}$) of the eight most recent RP intervals less than 150 milliseconds by 50 milliseconds or less. If so, the processor compares the P—P interval in the R—R interval under question with the P—P interval separating the final atrial event of the preceding R—R interval to the first atrial event of the R—R interval under question. If, as discussed above, the difference between the two PP intervals is greater than or equal to 30 milliseconds, the R—R interval under question is determined to likely contain a farfield R wave.

The processor keeps track of the number of R—R intervals out of a preceding series of intervals (e.g., 12 intervals) which likely contain a farfield R wave. This number (Far R Counter) is compared to a threshold value (Far R Threshold, e.g, 10) to determine whether it is likely that a heart rhythm which appears to have a high atrial rate is in fact the result of farfield R wave sensing.

An additional new diagnostic criterion employed by the device according to the present invention is a measurement of the degree of co-variance of measured R-P and R—R intervals. This diagnostic criterion is employed in conjunction with rules intended to identify the occurrence of atrial fibrillation or flutter. The processor determines the co-variance of R-P and R—R cycle lengths over a preceding series of a predetermined number of R—R intervals (e.g, 12) by subtracting from each measured RP interval, the previously measured RP interval to provide a first value (RPΔ) and by subtracting from each R—R interval, the value of the R—R interval immediately preceding it to provide a difference value (RRΔ). For each R—R interval, the value of RRΔ is subtracted from RPΔ, and the absolute value is stored. The sum of these absolute values over the preceding 10 R—R intervals (SumAbsDiffOfDeltas) is compared to a threshold value in conjunction with rules intended to identify the occurrence of atrial fibrillation or flutter and sinus tachycardia. If the value of some SumAbsDiffofDeltas exceeds a first recognition threshold, it is taken as evidence of the occurrence of atrial fibrillation and flutter. In the event that the SumAbsDiffOfDeltas is less than a second, lower threshold value, this is taken as evidence of the occurrence of sinus tachycardia.

Figure 11:
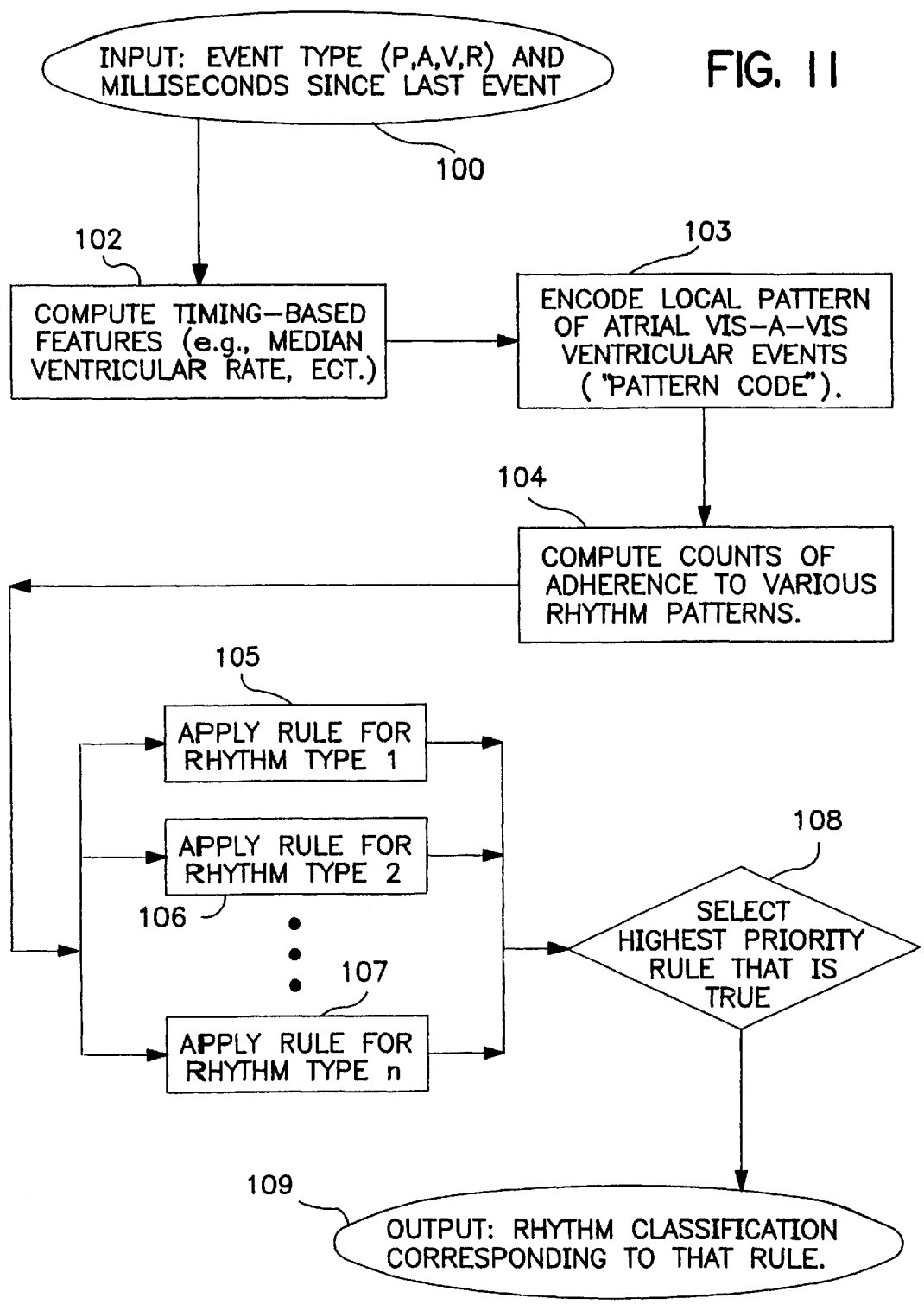
FIG. 11 is a functional flowchart illustrating the operation of the heart rhythm classification methodology employed by the present invention.

FIG. 11 illustrates the basic operation of a device according to the present invention, in response to the occurrence of atrial and ventricular events. In response to an atrial ventricular event at 100, the type of event is stored, and also a number of counts and values referred to above are updated. In particular, in response to an atrial or ventricular event, the processor stores information as to the P count, i.e. the number of atrial events received since the last ventricular event, and an R count, i.e. the count of the number of ventricular events received since the last atrial event, and R—R, R-P, P—P and P-R intervals, as appropriate. The processor maintains buffers in the RAM, in which the following information is stored: the 12 most recent P—P intervals are stored, the 12 most recent R—R intervals are stored, the 12 most recent absolute values of the differences between successive R-P and R—R intervals, as described above in conjunction with the generation of the SumAbsDiffOfDeltas value, the 8 immediately preceding R-P intervals, the 8 most recent P-R interval values, and the times of occurrence of atrial and ventricular events over the preceding 12 R—R intervals, employed in conjunction with the detection of farfield R waves, as discussed above. In addition, the processor also maintains a memory buffer of the bin indexes for the preceding 18 R—R intervals, as described above in conjunction with the computation of the RR modesum value and a buffer containing the number of R—R intervals over the preceding sequence of a programmable number of R—R intervals, which have durations less than FDI, as discussed above in conjunction with the detection criterion adapted from the Model 7219 PCD device.

At 102, the processor updates all timing based features associated with the occurrence of atrial and ventricular events, including all computations necessary to update the buffers described above, computation of all timing based values associated with the Model 7219 detection criteria described above, including updating of the value of VTEC, VFEC, the onset and stability counters, as well as updating the value of SumAbsDiffOfDeltas, the RR modesum value as described above, computation of the median values of the 12 preceding stored RR interval durations, computation of the median value of the stored preceding 12 PP intervals, as appropriate, and in the case of a ventricular event, updates the beat code for the R—R interval ending with the ventricular event.

In addition to these functions, in response to the occurrence of a ventricular event, the processor at 103 computes the corresponding pattern code, as described above, associated with the R—R interval ending with the ventricular event and at 104 updates the continuous recognition machine counters, as described above. The processor now has stored in RAM all information necessary to apply the hierarchial set of rules used to identify the particular type of rhythm under way.

At 105, 106, 107, the processor determines which of the various available rules have all of their respective clauses satisfied. As discussed above, one, more than one, or no rules may have their causes all satisfied. If more than one rule is true or "fires" the rule of highest priority is selected at 108, leading to a rhythm classification corresponding to that rule at 109. In response to the classification of the rhythm, the device delivers therapy or prevents delivery of therapy, depending upon the rhythm identified. In the absence of any rules being identified, the device withholds anti-tachycardia therapy. If the device is programmed to provide bradycardia backup pacing, it continues to do so. If not, the device simply continues to monitor the rhythm of the heart, until one or more rules fire.

In the context of the specific embodiment disclosed herein, several possible rhythm classifications are provided by the rule set. These include ventricular fibrillation, fast ventricular tachycardia, ventricular tachycardia, simultaneous ventricular and supraventricular tachycardia, atrial fibrillation or flutter, sinus tachycardia, AV nodal re-entrant tachycardia, normal sinus rhythm or "unclassified", indicating that no rules are "firing".

In conjunction with the present invention, 11 separate rules are employed to identify the various rhythm types listed above. These rules are in order of priority.
1. VF Rule
2. VT+SVT Rule
3. VT Rule
4. AF/A Flutter—first rule
5. AF/A Flutter—second rule
6. ST Rule
7. AVNT Rule
8. NSR Rule
9. VF Rule—7219

10. FVT Rule—7219
11. VT Rule—7219

Of the above rules, the AF/A Flutter rules, the ST rule, the AVNT rule and the NSR rule all prevent delivery of anti-tachyarrhythmia therapies. The remaining rules trigger delivery of therapies. As such, the hierarchial structure of the rule base is such that three lowest priority rules are provided for triggering therapy, superseded by four intermediate priority rules for inhibiting delivery of anti-tachyarrhythmia therapy, which in turn are superseded by three high priority rules, triggering delivery of anti-tachycardia therapy. This hierarchial rule structure is believed to be unique in the context of automated devices for triggering delivery of anti-tachycardia therapies.

The specific rules and their individual clauses are described in detail below, illustrating the interrelation of the various timing based and pattern based criteria described above.

1. VF Rule

The VF rule is the highest priority rule employed by the device. If it is met, it triggers delivery of the next scheduled ventricular fibrillation therapy, typically a high voltage defibrillation pulse. This rule has three clauses and is set true, or "fires" when all three clauses are satisfied. The first clause simply requires that ventricular fibrillation detection, as in the Model 7219, has been programmed on. The second clause requires that VFEC is greater or equal to VFNID, as discussed in conjunction with the VF detection criteria employed with the Model 7219 discussed above. An additional criterion, not present in the VF detection criterion employed by the Model 7219 is that the median value for the preceding 12 R—R intervals is less than a preset fast VT minimum cycle length, which may be programmable by the physician, or defined as a fixed value within the device. An appropriate value for this fast VT minimum cycle length is 240 milliseconds, indicating that the rate is too fast to be the result of ventricular tachycardia, and too fast to go untreated. Firing of the VF rule will supersede the firing of rules indicating the likely occurrence of atrial tachyarrhythmias, which would normally prevent delivery of therapy.

2. VT+SVT Rule

The second highest priority rule is intended to identify the simultaneous occurrence of ventricular tachycardia and supraventricular tachycardia. This rule contains seven clauses, all of which must be satisfied in order for the rule to be set true or "fire". The first clause requires that ventricular tachycardia detection as in the 7219 be enabled, and that the value of VTEC be greater than or equal to VTNID (as discussed above in conjunction with the Model 7219 detection criteria) or that VT detection is enabled with the rate stability feature described above in conjunction with the Model 7219 detection criteria is enabled.

The second clause requires that the far field R wave counter exceeds the far field R wave counter threshold, for example that 10 of the last 12 RR intervals are determined likely to contain farfield R waves. The third clause requires that the value of CRMedDT exceeds a recognition threshold, e.g. a count of eight.

The fourth clause requires that the value of CRMedDT exceeds the value of CRMedAF. The fifth clause requires that the median value of the 12 most recent RR intervals is less than TDI, as defined above in conjunction with the Model 7219 detection criteria, and is greater than or equal to the fast VT minimum cycle length described above in conjunction with the VF rule. The sixth and final clause of the VT+SVT rule requires that the value of RR modesum, as discussed above is unknown or that RR modesum is greater than or equal to a defined threshold value, e.g. 25%.

If all of these clauses are satisfied, the rule is set true and "fires" triggering delivery of the next scheduled fast ventricular tachycardia therapy, if available, or the next scheduled ventricular tachycardia therapy, in the event that separate fast and slow ventricular tachycardia therapies are not scheduled. Firing of the VT+SVT rule supersedes firing of any other rules, with the exception of the VF rule, described above.

3. VT Rule

The VT rule has six clauses which must be satisfied, in order for the rule to be set true. The first clause simply requires that ventricular tachycardia detection be enabled, as described above in conjunction with the VT+SVT rule. The second clause requires that the VFEC be greater or equal to VFNID or that the VFEC exceed or equal six and that the sum of the VFEC and VTEC exceeds VFNID with at least one of the last eight R—R intervals have a duration less than FDI or $FTDI_{min}$, which ever is smaller, as discussed above in conjunction with the Model 7219 detection criteria.

The third clause requires that CRMAVNT exceeds its corresponding recognition threshold, e.g. eight. The fourth clause requires that CRMST be less than its corresponding recognition threshold, e.g. eight. The fifth clause requires that the median R—R interval over the preceding sequence of 12 R—R intervals is less than or equal to the fast VT minimum cycle length, discussed above in conjunction with the VF and VT+SVT rules. The sixth clause requires that RR modesum be unknown or that it be less or equal to a set threshold, e.g., 87.5%. If all clauses are satisfied, the rule is set true or "fires". If it is the highest priority firing rule, delivery of the next scheduled fast ventricular tachycardia therapy, if enabled, is triggered. If separate fast ventricular tachycardia and slow ventricular tachycardia therapies are not enabled, the next available ventricular tachycardia therapy is triggered.

4. AF/Atrial Flutter—First Rule

Due to the importance of distinguishing rapid ventricular rhythms due to atrial fibrillation or flutter from tachycardias of ventricular origin, two separate rules are provided for identifying the likely occurrence of atrial fibrillation or flutter (or other atrial tachycardia). The first of these two rules has three clauses which must be satisfied in order for the rule to be met. The first clause requires that the value of CRMAL is greater than or equal to its corresponding recognition threshold, e.g. eight. The second clause requires that the median value of the last 12 R—R intervals is less than TDI, as described in conjunction with the Model 7219 detection criteria and the third rule is that RR modesum is less than the count of farfield R waves over the preceding 12 intervals divided by 16 and subtracted from a preset value e.g. 1.5. The third clause of this rule is intended to determine whether the rate of ventricular events is more variable than would be expected if simultaneous atrial and ventricular tachycardias are occurring. This clause reflects an empirically derived relationship, and is the only multidimensional discriminate function employed in the set of rules provided by the present invention. If all three clauses are met, the rule is set true or "fires". If this is the highest priority firing rule, delivery of anti-tachyarrhythmia therapy is prevented even if lower priority ventricular tachycardia or ventricular fibrillation rules are met while the rule is firing.

5a. AF/Atrial Flutter—Second Rule—First embodiment

The second rule directed toward detection of the occurrence of atrial fibrillation or flutter (or other atrial tachycardia) also has three clauses which must be met. The first clause requires that the number of R—R intervals identified as likely containing sensed farfield R waves, out of the preceding 12 R—R intervals, be less than a threshold value, e.g. 10. The second clause requires that the median value of the P—P interval, over the preceding 12 R—R intervals be known, and that it be less than a preset value, e.g. 87.5% of the corresponding median R—R value, over the preceding 12 intervals. The third clause is a complex rule which requires that CRMedAF exceed its corresponding recognition threshold (e.g. 8) and that one of the following subclauses be met. The first subclause requires that RR modesum be either unknown or that it be less than a preset mode sum threshold, e.g. 50%. The second subclause requires that the value of SumAbsDiffOfDeltas be greater than or equal to a predefined threshold, e.g. 2,000 milliseconds. The third subclause requires that CRMedDT be less than its corresponding recognition threshold, e.g. eight. If any of these three subclauses are met in conjunction with CRMedAF exceeding or equalling its recognition threshold, the third clause of this rule is satisfied. If all three clauses of the rule are satisfied, the rule is set true or "fires". If this rule is the highest firing priority rule, delivery of anti-tachycardia therapies is prevented.

5b. AF/Atrial Flutter—Rule 2—Second embodiment

An alternative version of the second AF/Atrial Flutter rule dispenses with the continuous recognition machine of FIG. 8 and substitutes a simpler counter (AF evidence counter) which counts up when there is evidence of atrial fibrillation during an R—R interval, counts down when there is contrary evidence and remains unchanged when the situation is ambiguous. In the context of this second embodiment of the second AF/Atrial Fibrillation rule, the AF evidence counter is considered to be met or to be "firing" when it reaches a count of seven. and continues to "fire" thereafter until its count is decremented to five or less. The counter is incremented or decremented as follows.

If the P count for the preceding R—R interval is greater than two, the AF evidence counter is incremented by one. If the P-count is two, the counter is incremented by one unless the current beat code is the same as the previous beat code and the R—R interval has been identified as likely containing a far-field R-wave, as discussed above, in which case the counter is not incremented or decremented. If the P count is one, the counter is decremented by one only if the current beat code is the same as the previous beat code, and otherwise is neither incremented or decremented. If the P count is zero, the counter is decremented by one.

The second embodiment of the second AF/Atrial Flutter rule has four clauses which must be met for the rule to "fire". The first clause requires that the number of R—R intervals identified as likely containing sensed farfield R waves, out of the preceding 12 R—R intervals, be less than a threshold value, e.g. 10. The second clause requires that the median value of the P—P interval, over the preceding 12 R—R intervals be known, and that it be less than a preset value, e.g. 93.75% of the corresponding median R—R value, over the preceding 12 intervals. The third clause is a complex rule which requires that the AF evidence counter be firing and that one of the following subclauses be met. The first subclause requires that RR modesum be either unknown or that it be less than a preset mode sum threshold, e.g. 50%. The second subclause requires that the value of SumnAbsDiffOfDeltas be greater than or equal to a predefined threshold, e.g. 2,000 milliseconds. The third subclause requires that CRMedDT be less than its corresponding recognition threshold, e.g. eight. If any of these three subclauses are met in conjunction with CRMedAF exceeding or equaling its recognition threshold, the third clause of this rule is satisfied. If all three clauses of the rule are satisfied, the rule is set true or "fires". If this rule is the highest firing priority rule, delivery of anti-tachycardia therapies is prevented.

6. ST Rule

This rule is directed toward recognition of sinus tachycardia, and includes four clauses which must be satisfied in order for the rule to fire. The first clause requires that CRMST exceed its corresponding recognition threshold, e.g. 8. The second rule requires that the median value of the preceding 12 R—R intervals be greater than or equal to the value of FDI as discussed above in conjunction with the model 7219 detection criteria. The third rule requires that the median R—R interval value be less than TDI as described above in conjunction with the 7219 detection criteria. The fourth rule requires that the value of SumAbsDiffOfDeltas be less than or equal to a preset threshold, e.g. 500 milliseconds. It should be noted that this threshold is less than the threshold to which some SumAbsDiffOfDeltas is compared in conjunction with the second AF/A flutter rule, described above. If all clauses are satisfied, the rule is set true or "fires". If the ST Rule is the highest priority rule firing, delivery of anti-tachycardia therapies is prevented.

7. AVNT Rule

This rule is directed toward detection of AV nodal re-entrant tachycardia. The rule includes three clauses, each of which must be satisfied in order for the rule to fire. The first clause requires that CRMAVNT exceed its corresponding threshold value, e.g. 8. The second clause requires that the median value of the preceding 12 R—R intervals be greater than or equal to the fast VT minimum cycle length, described above in conjunction with the VF rule. The third clause requires that the median R—R interval value be less than TDI, as discussed above in conjunction with the Model 7219 detection criteria. The fourth clause requires that RR modesum is either unknown, or if known, is less than a preset threshold, e.g. 25%. If all four clauses are satisfied, the rule is set true or "fires". If it is the highest priority firing rule, it prevents delivery of ventricular anti-tachycardia therapies.

8. NSR Rule

This rule is directed toward detection of a normal sinus rhythm, and includes two clauses which must be satisfied in order for the rule to be set true. The first clause requires that CRMST be greater than or equal to its corresponding recognition threshold, e.g. 8. The second clause requires that the median value of the preceding 12 R—R intervals is greater than or equal to TDI as defined in conjunction with the Model 7219 detection criteria. If this rule is the highest priority firing rule, delivery of ventricular anti-tachycardia therapy is prevented.

The final three rules are the ventricular fibrillation and tachycardia detection rules adapted from the Model 7219, as discussed above.

9. VF Rule—7219

This rule corresponds to the detection criteria for ventricular fibrillation as set forth above in conjunction with the description of the Model 7219 device. If VF is detected using these criteria, the rule is set true and "fires" if it is the highest firing rule, it triggers delivery of the next scheduled ventricular fibrillation therapy.

10. Fast VT Rule—7219

This rule simply restates all of the fast ventricular tachycardia detection criteria provided in the Model 7219 device, as discussed above. If fast VT detection is programmed on, and this rule is the highest firing rule, it triggers delivery of the next scheduled fast VT therapy. This rule should be considered to include a detection of fast ventricular tachycardia following provisional detection of VT and/or detection of fast ventricular tachycardia following provisional detection of VF, the use of the combined count criterion for provisional detection, and all other features associated with detection of fast ventricular tachycardias as embodied in the Model 7219 device.

11. VT Rule—7219

This rule simply restates all of the ventricular tachycardia detection criteria provided in the Model 7219 device, as discussed above. In the event that this rule is the highest firing rule. it triggers delivery of the next scheduled VT therapy. This rule should be considered to include detection of ventricular tachycardia in the event that fast ventricular tachycardia detection following a provisional detection of ventricular tachycardia is not programmed on, as confirmation of (slow) ventricular tachycardia following provisional detection of VT. Detection of VT, detection of fast ventricular tachycardia via initial detection of VF, including the use of the combined count criterion for initial detection, and all other features associated with detection of ventricular tachycardia as embodied in the Model 7219 device.

In conjunction with above rule set, it should be understood that in the event that a rule triggering delivery of a ventricular tachycardia therapy fires, subsequent firing of a rule indicative of the occurrence of a supraventricular tachycardia cannot occur, as the pattern grammar, and/or other timing criteria cannot possibly be met after initiation of anti-tachycardia therapy. However, it is certainly possible for a rule indicating the occurrence of a ventricular tachyarrhythmia to fire while a rule indicative of the occurrence of a supraventricular tachycardia is firing. In such case, the highest priority firing rule dominates. It should also be understood that rules 1–8 above are "sticky"rules, meaning that once a rule has fired, it will continue to fire until one or more clauses of the rule are not satisfied for a sequence of a predetermined number of R—R intervals. A nominal value for this predetermined number of R—R intervals is three, however, it is envisioned that the parameter may be programmable by the physician. This feature is intended to prevent a temporary violation of one of the clauses of a rule, for one or two beats, to override the firing of the rule. This is particularly important in the context of the rules intended to detect the likely occurrence of atrial tachycardias, where a one or two beat failure of the rule to be met could well result in the delivery of a ventricular anti-tachycardia therapy, in conjunction with the firing of a lower priority VT or VF detection rule, resulting in inappropriate delivery of ventricular anti-tachycardia therapy.

In conjunction with commercial embodiments of devices according to the present invention, it is anticipated that selecting which of the various available rules are to be activated in the device may prove an overwhelming task for the physician. As such, it is proposed that selection the available sets of rules be limited to a few, predefined sets of rule combinations. For example, in conjunction with the specific set of rules disclosed above, it is proposed that the physician be presented with the basic detection criteria associated with the Model 7219 device as described above, in conjunction with three optional additional sets of detection criteria. Each of these options may be described in terms of the type of atrial arrhythmia which is intended to be detected, for prevention of delivery of therapy. The three options are as follows.

Option 1. Atrial fibrillation/flutter/tachycardia

If this option is selected by the physician, the purpose is to provide the device with the ability to detect the occurrence of atrial fibrillation, atrial flutter or atrial tachycardia, and withhold the delivery of ventricular therapies. If this option is selected, in addition to the Model 7219 detection criteria, Rules 1–5 and 8 are activated, with Rules 6 and 7 left deactivated. Alternatively, the physician may be provided with the alternative of simply turning these rules on, for diagnostic purposes only, so that they do not override the effect of the Model 7219 detection set. This option is particularly valuable in that it will allow the physician to determine whether or not this particular combination of rules provides a workable detection methodology for the patient in whom the device is implanted.

Option 2. Sinus Tachycardia

This option is intended to allow the physician to program the device to prevent delivery of ventricular anti-tachycardia therapies in the presence of sinus tachycardia. If this option is selected, Rule 1, 2, 3, 6, and 8 are activated in addition to the Model 7219 detection criteria. As in the case of the above rule, activating these rules for diagnostic purposes, while preventing them from overriding the Model 7219 detection criteria should also be possible.

Option 3. AVNT Detection

The third option is directed towards allowing the physician to optimize the device to prevent triggering of ventricular anti-tachyarrhythmia therapy in the presence of AV nodal re-entrant tachycardia. If this option is selected, Rules 1, 2, 3, 7 and 8 are activated in conjunction with the detection criteria associated with the Model 7219 device. Again, activation of these rules may be in a passive mode only, if such that they do not override the detection criteria of the Model 7219 device.

In conjunction with the selectable options, it should be understood that the effect of selecting multiple options is additive, such that if all three options are selected, all of Rules 1–8 are activated. It should also be noted that under this proposed approach to selecting sets of rules to be activated, that the highest priority rules 1, 2, and 3 which trigger delivery of therapy are not activated in the absence of activation of one or more of intermediate priority rules 4–8, which inhibit delivery of anti-tachycardia therapy. The reason for this is that the higher priority rules 1–3 set forth more strict requirements for detection of fibrillation and tachycardia than the Model 7219 detection rules, and are thus unnecessary, in the absence of intermediate priority rules 4–8, capable of overriding the 7219 detection criteria.

While the above rule set is described in terms of initial detection of a tachyarrhythmia, such a prioritized rule system may also be employed in conjunction with redetection of a tachyarrhythmia or in detection of a change of type of tachyarrhythmia. However, due to the complexities of such a system, it is proposed that as a practical matter, the device may simply be programmed such that following delivery of an initial tachycardia therapy, detection of termination of the arrhythmia and redetection of the arrhythmia be conformed to that employed in the Model 7219, for the sake of ease of use and simplicity. In such an embodiment, delivery of an initial anti-tachyarrhythmia therapy will result in disablement of Rules 1–8 until subsequent detection of termination of the detected arrhythmia, following which Rules 1–8, as selected by the physician, may be reactivated.

The above disclosure sets forth a device in which sensed events in the atrium and ventricle are used to control delivery of therapy to treat ventricular tachyarrhythmias. However, the basic hierarchial, rule-based arrhythmia detection methodology set forth is believed equally applicable to devices which deliver arrhythmia therapies directed towards treatment of atrial arrhythmias, or towards devices which are intended to treat both atrial and ventricular arrhythmias.

Identification of the origin of the arrhythmia and withholding of therapy from one or more chambers of the heart, in response to an accurate diagnosis of the origin of the arrhythmia is equally valuable in such devices. Furthermore, it seems likely that commercial embodiments of such a device will require the use of a microprocessor in order to perform the numerous calculations and analysis steps required, it is within the realm of possibility that some or all of the detection criteria provided by the microprocessor in the above disclosure might instead be provided by means of a full custom, integrated circuit, particularly a circuit in which a state counter is employed instead of stored software, in order to control sequential operation of the digital circuitry, along the general lines of the circuits disclosed in U.S. Pat. No. 5,088,488, issued to Markowitz et al. and U.S. Pat. No. 5,052,388, issued to Sivula et al., both of which are incorporated herein by reference in their entireties.

Furthermore, while the above disclosure is specifically related to devices which trigger delivery of electrical therapies to treat tachyarrhythmias, it is also believed that the various detection criteria and hierarchal rule base system disclosed above might usefully be employed in devices which deliver other forms of therapy in response to detection of tachyarrhythmias, including delivery of anti-arrhythmia drugs. Thus, the above description should be considered exemplary, rather than limiting with regard to the interpretation of the following claims.

In conjunction with the above disclosure, we claim:

1. An anti-arrhythmia device, comprising:
   means for sensing depolarizations of heart tissue;
   means for defining a set of prioritized rules which may be simultaneously met, including a first rule indicating the need for delivery of anti-arrhythmia therapy and a second rule which indicates that an anti-arrhythmia therapy is not needed, each of said prioritized rules defining at least one criterion based upon characteristics of said sensed depolarizations of heart tissue, each of said prioritized rules being met responsive to a said criterion of said prioritized rule being met;
   analyzing means for determining which of said prioritized rules are met, comprising means for determining whether sensed depolarizations continue to meet a said criterion of one of said prioritized rules over a sequence of said sensed depolarizations and means responsive to said sensed depolarizations continuing to meet said criterion of said one of said prioritized rules over said sequence of sensed depolarizations for determining which of said prioritized rules are met;
   means for determining the highest priority one of said prioritized rules which are met;
   means responsive to the first rule being the highest priority rule met, for delivering an anti-arrhythmia therapy; and
   means responsive to the second rule being the highest priority rule met, for preventing delivery of an anti-arrhythmia therapy.

2. A device according to claim 1, wherein a said criterion for meeting one of said prioritized rules comprises a said criterion for meeting another of said prioritized rules.

3. A device according to claim 1, wherein a said criterion for meeting one of said prioritized rules comprises the degree to which a said criterion of another of said prioritized rules is met.

4. A device according to claim 1, wherein a said criterion for meeting one of said prioritized rules comprises failure of said sensed depolarizations to meet another of said prioritized rules.

5. An anti-arrhythmia device, comprising: means for sensing depolarizations of heart tissue;
   means for defining a set of prioritized rules which may be simultaneously met, including a first rule indicating the need for delivery of anti-arrhythmia therapy and a second rule which indicates that an anti-arrhythmia therapy is not needed, each of said prioritized rules defining at least one criterion based upon characteristics of said sensed depolarizations of heart tissue, each said prioritized rule being met responsive to a said criterion of said prioritized rule being met, wherein a said criterion for meeting one of said prioritized rules comprises a said criterion for meeting another of said prioritized rules;
   means for analyzing said characteristics of said sensed depolarizations to determine which of said prioritized rules are met;
   means for determining the highest priority one of said prioritized rules which are met;
   means responsive to said first rule being the highest priority rule met, for delivering an anti-arrhythmia therapy; and
   means responsive to said second rule being the highest priority rule met, for preventing delivery of an anti-arrhythmia therapy.

6. An anti-arrhythmia device, comprising:
   means for sensing depolarizations of heart tissue;
   means for defining a set of prioritized rules which may be simultaneously met, including a first rule indicating the need for delivery of anti-arrhythmia therapy and a second rule which indicates that an anti-arrhythmia therapy is not needed, each of said prioritized rules defining at least one criterion based upon characteristics of said sensed depolarizations of heart tissue, each said prioritized rule being met responsive to a said criterion of said prioritized rule being met, wherein a said criterion for meeting one of said prioritized rules comprises the degree to which a said criterion of another of said prioritized rules is met;
   means for analyzing said characteristics of said sensed depolarizations to determine which of said prioritized rules are met;
   means for determining the highest priority one of said prioritized rules which are met;
   means responsive to said first rule being the highest priority rule met, for delivering an anti-arrhythmia therapy; and
   means responsive to said second rule being the highest priority rule met, for preventing delivery of an anti-arrhythmia therapy.

7. An anti-arrhythmia device, comprising:
   means for sensing depolarizations of heart tissue;
   means for defining a set of prioritized rules which may be simultaneously met, including a first rule indicating the need for delivery of anti-arrhythmia therapy and a second rule which indicates that an anti-arrhythmia therapy is not needed, each of said prioritized rules defining at least one criterion based upon characteristics of said sensed depolarizations of heart tissue, each said prioritized rule being met responsive to a said criterion of said prioritized rule being met, wherein a said criterion for meeting one of said prioritized rules comprises failure of said sensed depolarizations to meet another of said prioritized rules;
   means for analyzing said characteristics of said sensed depolarizations to determine which of said prioritized rules are met;

means for determining the highest priority one of said prioritized rules which are met;

means responsive to said first rule being the highest priority rule met, for delivering an anti-arrhythmia therapy; and means responsive to said second rule being the highest priority rule met, for preventing delivery of an anti-arrhythmia therapy.

* * * * *